US009545329B2

(12) United States Patent
Salama (10) Patent No.: US 9,545,329 B2
(45) Date of Patent: Jan. 17, 2017

(54) FLOW CONTROL AND COLLECTION DEVICE

(75) Inventor: Fouad A. Salama, Temecula, CA (US)

(73) Assignee: International Medical Technology, Temecula, CA (US)

( * ) Notice: Subject to any disclaimer, the term of this patent is extended or adjusted under 35 U.S.C. 154(b) by 175 days.

(21) Appl. No.: 13/031,379

(22) Filed: Feb. 21, 2011

(65) Prior Publication Data

US 2012/0215188 A1 Aug. 23, 2012

(51) Int. Cl.
  *A61F 5/44* (2006.01)
  *A61F 5/445* (2006.01)
  *A61F 5/448* (2006.01)

(52) U.S. Cl.
  CPC ............... *A61F 5/445* (2013.01); *A61F 5/448* (2013.01); *A61F 2005/4483* (2013.01); *A61F 2005/4486* (2013.01)

(58) Field of Classification Search
  CPC ........ A61F 5/445; A61F 5/448; A61F 5/4405; A61F 5/4408; A61F 5/4407; A61F 2005/4486; A61F 2005/4483; A61F 2005/4455; Y10T 403/40; Y10T 29/49922
  USPC .................................................. 604/335, 332
  See application file for complete search history.

(56) References Cited

U.S. PATENT DOCUMENTS

| 2,008,330 A * | 7/1935 | McGuigan ................. 301/35.56 |
| 2,730,381 A * | 1/1956 | Curtiss ..................... 285/148.23 |
| 3,900,795 A * | 8/1975 | Larsen et al. ................. 324/537 |
| 4,419,100 A | 12/1983 | Alexander |
| 4,721,508 A * | 1/1988 | Burton .................... A61F 5/445 604/103.03 |
| 4,799,929 A | 1/1989 | Knowles |
| 4,846,798 A | 7/1989 | Holtermann et al. |
| 4,911,699 A | 3/1990 | Fenton |
| 5,185,008 A | 2/1993 | Lavender |
| 5,242,373 A * | 9/1993 | Scott et al. ....................... 600/7 |

(Continued)

FOREIGN PATENT DOCUMENTS

EP 0 689 810 A2 1/1996

OTHER PUBLICATIONS

International Medical Technology, Inc., PCT/US2012/025225 filed Feb. 15, 2012, "Notification of Transmittal of the International Search Report and the Written Opinion of The International Searching Authority" mailed Jun. 20, 2012.

*Primary Examiner* — Tatyana Zalukaeva
*Assistant Examiner* — Ariana Zimbouski
(74) *Attorney, Agent, or Firm* — McKee, Voorhees & Sease, PLC (57) ABSTRACT

A flow control and collection system includes a flow control device having a tubular member in which an inflatable balloon is positioned about the circumference of the interior side wall for closing the passageway to movement of matter and liquid when the balloon is expanded and allowing flow when the balloon is contracted against the side wall to which it is attached. The flow control device includes an adapter at the outer end of the tubular member having one or more interlocking features. A waste collection bag has a sealed body with at least one opening and a flow control device adapter at the opening having one or more counterpoising interlocking features to removably lock the adapters together and passes waste material and liquid through the flow control device into the waste collection bag.

11 Claims, 8 Drawing Sheets

(56) References Cited

U.S. PATENT DOCUMENTS

| | | | |
|---|---|---|---|
| 5,261,898 A * | 11/1993 | Polin | A61F 2/0013 604/327 |
| 5,269,774 A * | 12/1993 | Gray | 604/343 |
| 5,312,381 A | 5/1994 | Brooks | |
| 5,647,861 A | 7/1997 | Steer et al. | |
| 5,690,623 A | 11/1997 | Lenz et al. | |
| 5,693,035 A | 12/1997 | Leise, Jr. et al. | |
| 5,730,735 A | 3/1998 | Holmberg et al. | |
| 5,947,941 A | 9/1999 | Leise, Jr. et al. | |
| 6,135,986 A | 10/2000 | Leisner et al. | |
| 6,328,719 B1 | 12/2001 | Holtermann et al. | |
| 6,432,093 B1 | 8/2002 | Shiina | |
| 6,485,476 B1 | 11/2002 | von Dyck et al. | |
| 6,659,988 B1 | 12/2003 | Steer et al. | |
| 6,802,831 B2 | 10/2004 | Plass et al. | |
| 7,001,367 B2 | 2/2006 | Arkinstall | |
| 7,087,042 B2 | 8/2006 | Montgomery | |
| 7,160,275 B2 | 1/2007 | Falconer | |
| 7,179,245 B2 | 2/2007 | Giori | |
| 7,468,056 B2 | 12/2008 | Burt | |
| 7,553,273 B2 | 6/2009 | Ferguson et al. | |
| 7,556,707 B2 | 7/2009 | Giori | |
| 7,604,622 B2 | 10/2009 | Pedersen et al. | |
| 2002/0077611 A1 * | 6/2002 | von Dyck et al. | 604/333 |
| 2003/0220621 A1 * | 11/2003 | Arkinstall | 604/335 |
| 2003/0236509 A1 | 12/2003 | Silvestrini | |
| 2005/0234424 A1 * | 10/2005 | Besing et al. | 604/500 |
| 2006/0206069 A1 | 9/2006 | Cline | |
| 2007/0123832 A1 * | 5/2007 | Cline et al. | 604/335 |
| 2007/0198034 A1 | 8/2007 | Ortiz et al. | |
| 2008/0045781 A1 * | 2/2008 | Salama | 600/29 |
| 2008/0215001 A1 * | 9/2008 | Cowe | 604/110 |
| 2009/0043151 A1 * | 2/2009 | Gobel | 600/31 |
| 2009/0216206 A1 | 8/2009 | Nishtala et al. | |
| 2009/0227970 A1 | 9/2009 | Nishtala et al. | |
| 2009/0227971 A1 | 9/2009 | Nishtala et al. | |
| 2009/0247969 A1 | 10/2009 | Nishtala et al. | |
| 2010/0069859 A1 * | 3/2010 | Weig | 604/335 |
| 2010/0174253 A1 | 7/2010 | Cline et al. | |
| 2010/0222754 A1 | 9/2010 | Nishtala et al. | |
| 2010/0280489 A1 | 11/2010 | Nishtala et al. | |

* cited by examiner

FLOW CONTROL AND COLLECTION DEVICE

BACKGROUND OF THE INVENTION

Persons requiring ostomy procedures or being incontinent have need for a flow control and collection device that will not leak or accidentally separate, and is simple to install, operate and remove.

SUMMARY OF THE INVENTION

The flow control and collection device of this invention meets the needs of persons having had an ostomy procedure to address incontinency issues, or are fecally incontinent. The flow control and collection devices of this invention can be positioned in a body opening such as a stoma or around the anus. For example, persons requiring a colostomy or ileostomy have need for a flow control and collection device of the present invention.

In one aspect of the invention, a flow control and collection system for human excretions is disclosed. The flow control device includes a tubular member having inner and outer ends interconnected by a passageway adapted for insertion into a body opening. An adapter at the outer end of the tubular member has one or more interlocking features. A collection bag that has a sealed body and at least one opening also includes a adapter having one or more counterpoising interlocking features to removably lock the device and bag adapters together.

A device providing flow control for human excretions is also disclosed. The device includes a tubular member having inner and outer ends connected by a passageway and the inner end adapted for insertion into a body opening. An adapter is included at the outer end of the tubular member having a plurality of radially spaced interlocking features formed in the adapter.

A bag for collecting human excretions is also disclosed. The bag includes a sealed body having at least one opening and an adapter attached to the body around the opening. The adapter includes a generally planar surface and a plurality of radially spaced interlocking features. The interlocking features removably lock the bag to a device having an inner end adapted for insertion into a body opening.

In another aspect of the invention, a flow control device for human excretions is disclosed. The device includes a tubular member having inner and outer ends interconnected by a passageway. The tubular member has a discontinuous side wall and the inner end of the tubular member is adapted for surgical attachment at a body opening. The device also includes a plurality of tube diameter adjustment points spaced opposite one another on opposing sides of the discontinuity in the side wall and a tether between opposing adjustment points to adjust the diameter of the passageway to the size of the body opening.

DETAILED DESCRIPTION OF THE PREFERRED EMBODIMENTS

Figure 1:
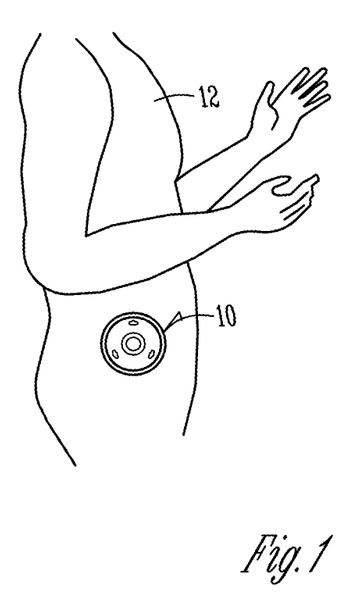
FIG. 1 is a fragmentary side view of a flow control device of this invention being positioned in a body opening of a person.

The flow control device of this invention is referred to generally in FIG. 1 by the reference numeral 10 and is shown positioned in a body opening, such as a stoma, on a the side of a person 12. The device 10 may be positioned in another body opening, such as the rectum of the person 12. The device 10 may be used, for example, by those having had a colostomy or ileostomy.

Figure 2A:
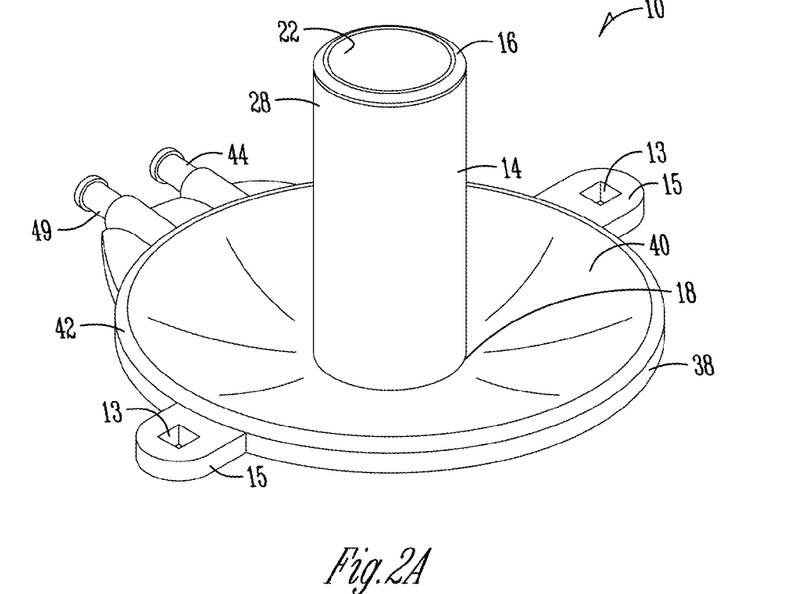
FIGS. 2A-B are perspective views of embodiments of the flow control device shown in FIG. 1.
Figure 2B:
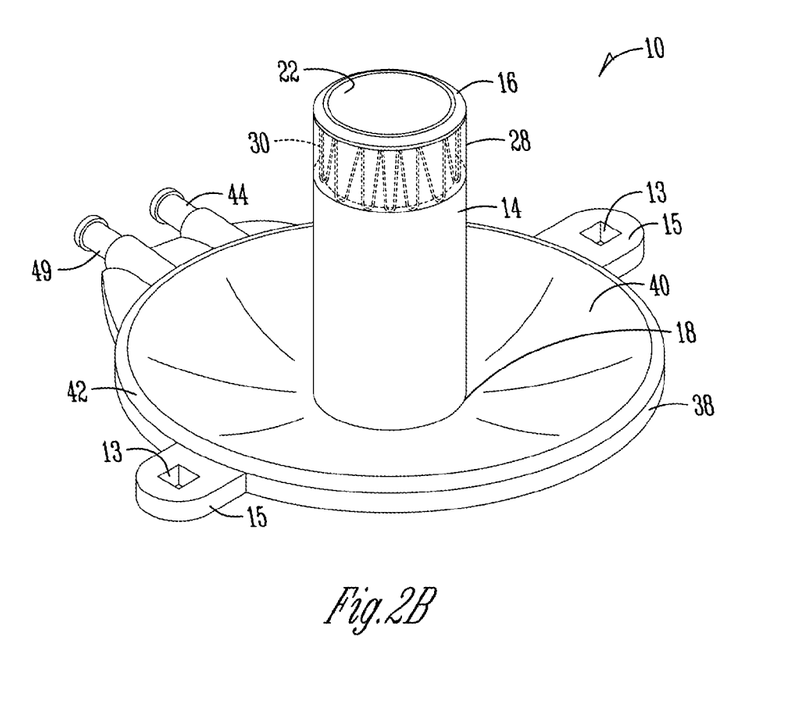

In FIGS. 2A-B, the flow control device 10 includes a tubular body member 14 having inner and outer ends 16 and 18, and on opposite sides of a body opening 19 (see FIG. 3) when installed. The tubular body member 14 may include one or more wall stiffeners to support the tubular member 14 against collapsing. In one aspect of the invention, the tubular member 14 includes an internal wall stiffener such as a rigid tube enclosed by the inner and outer skins of the tubular member 14. One example of a rigid tube includes polycarbonate tubing, or other tubing of sufficient strength to prevent the tubular member 14 from collapsing. Other types of stiffeners include the wire frame 30 discussed below. A wafer 42 in the form of a flange is connected to the outer end 18 of the tubular member 14. The inner surface 40 of wafer 42 may include a concave profile, with the depth of the profile decreasing from proximate the outer end 18 of the tubular member 14 outward to the outer peripheral edge of the wafer 42. The concavity of the inner surface 40 of wafer 42 prevents the inner surface 40 of wafer 42 from compressing or putting pressure on the tissue or mucosa 17 around the body opening 19, such as would be present in the case of a colostomy or ileostomy. A device adapter 38 is included on the side of wafer 42 opposite the inner surface 40 and further described below. The device adapter 38 includes a pair of ears 15 extending generally perpendicularly outward from the outer peripheral edge of the adapter 38. Each ear 15 includes an attachment point 13, such as a hole extending through the ear 15. An ostomy belt, such as are well known in the art, may be used to strap the device 10 to the person 12 by hooking ends of the belt to the attachment points 13.

Figure 3:
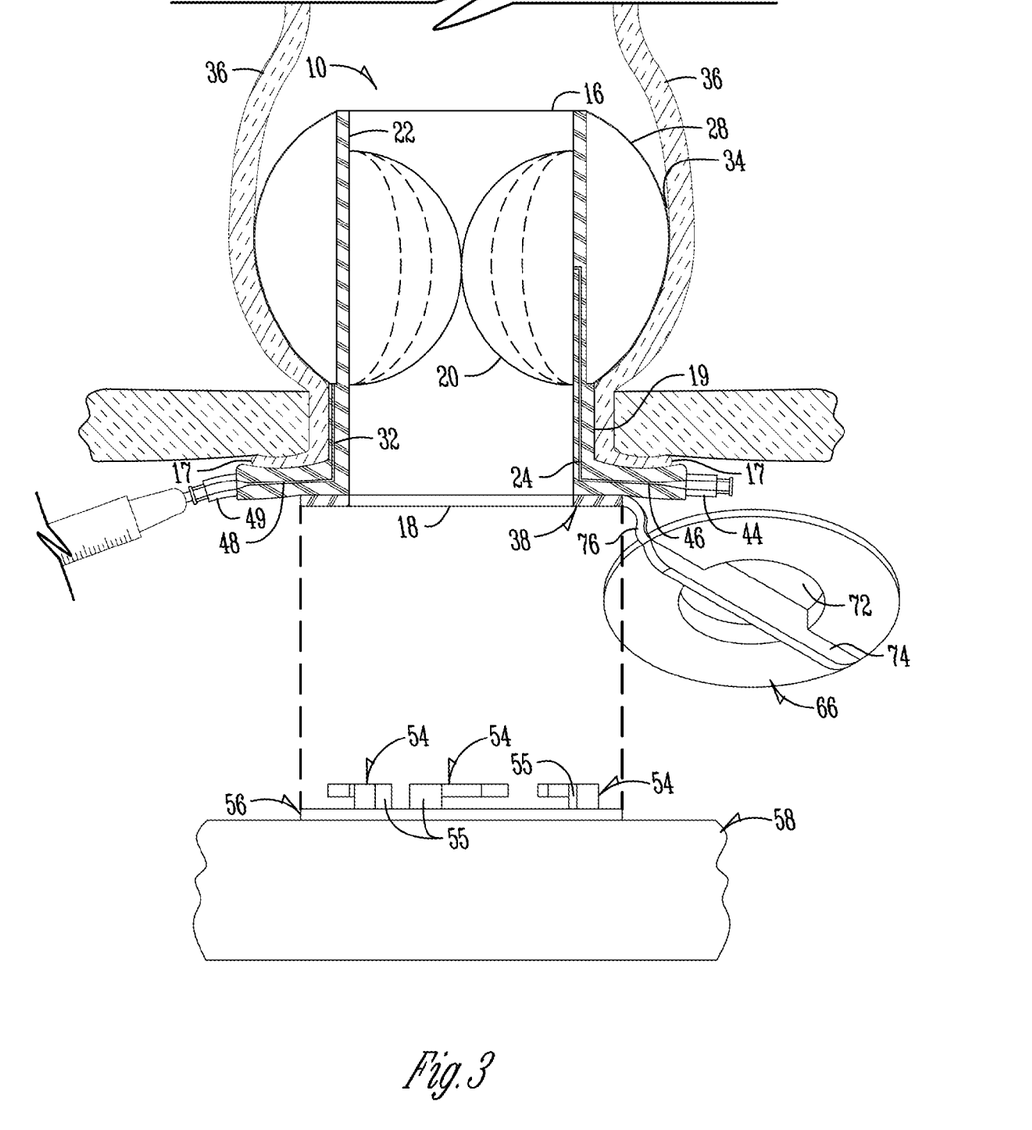
FIG. 3 is a cross-sectional view of a flow control device positioned in a body opening.

In FIG. 3, a balloon valve 20 is attached to the interior side wall 22 of the tubular member 14 and is inflated and deflated through a passageway 24 in the tubular member side wall 22. The balloon valve 20 is attached radially (i.e., 360 degrees) about the interior side wall 22 of the passageway 24. When the valve 20 is inflated, the balloon expands radially inward away from the interior side wall 22 of the passageway 24 toward the center of the passageway 24 in sealing engagement with itself. The balloon valve 20 seals closed the passageway 24 to prevent the flow of matter and fluid through the passageway 24 when the balloon valve 20 is inflated. The balloon valve 20 of the present invention is shown and described in a commonly owned application, application Ser. No. 11/464,686 filed Aug. 15, 2006, incorporated by reference herein in its entirety.

An expandable membrane 28 is attached at the inner end 16 of the tubular member 14, and in one aspect of this invention the interior side wall 22 is supported against being collapsed when the membrane 28 is inflated by a wire frame 30 (see FIG. 2B). The wire frame 30 is preferably positioned within the interior side wall 22 or secured to the interior side wall 22 to provide stiffness and rigidity to at least that portion of the side wall 22 supporting the pressure resulting from expansion of the expendable membrane 28 as shown in FIG. 3. In the case where the body opening 19 is generally smaller (e.g., such as with an ileostomy opening or chronic colostomy patients) the wire frame 30 may be collapsed or pinched to reduce the diameter of the inner end 16 of the tubular member 14 to facilitate insertion within a smaller body opening. The wire frame 30 may be configured to hold the collapsed position for an increment of time (e.g., the time needed to fully insert the inner end 16 in the body opening 19) and resume or expand to its original, pre-collapsed position after the increment of time has elapsed. For example, the wire frame 30 may include a memory which causes it to return to its original, pre-collapsed position from a collapsed or pinched position. After insertion of the device 10 and the wire frame 30 resuming its original, pre-collapsed position, the wire frame 30 supports the interior side wall 22 or tubular member 14 against collapsing when the expandable membrane 28 is inflated. In one aspect of the invention, the wire frame 30 comprises a nickel titanium alloy, such as Nitinol, having one or more memorized positions. The wire frame 30 may also be stainless steel, such as surgical grade stainless steel. Embodiments of this invention using the expandable membrane 28 with or without the wire frame 30 are contemplated. For example, the device 10 could include other types of stiffeners, such as those discussed above, to prevent the tubular member 14 from collapsing. As passageway 32 in the side wall of the tubular member 14 connects with the expandable membrane 28, the pressure applied to the expandable membrane 28 may of course vary as required to form a seal at the interface 34 between the expandable membrane 28 and the interior wall 36 surrounding the body opening 19 and retain the device 10 in the opening 19. For example, in the case of a colostomy or ileostomy, the expendable membrane 28 may be expanded to form a seal at the interface 34 between the interior wall surface 36 of the intestine and the expendable membrane as shown in FIG. 3.

Figure 4:
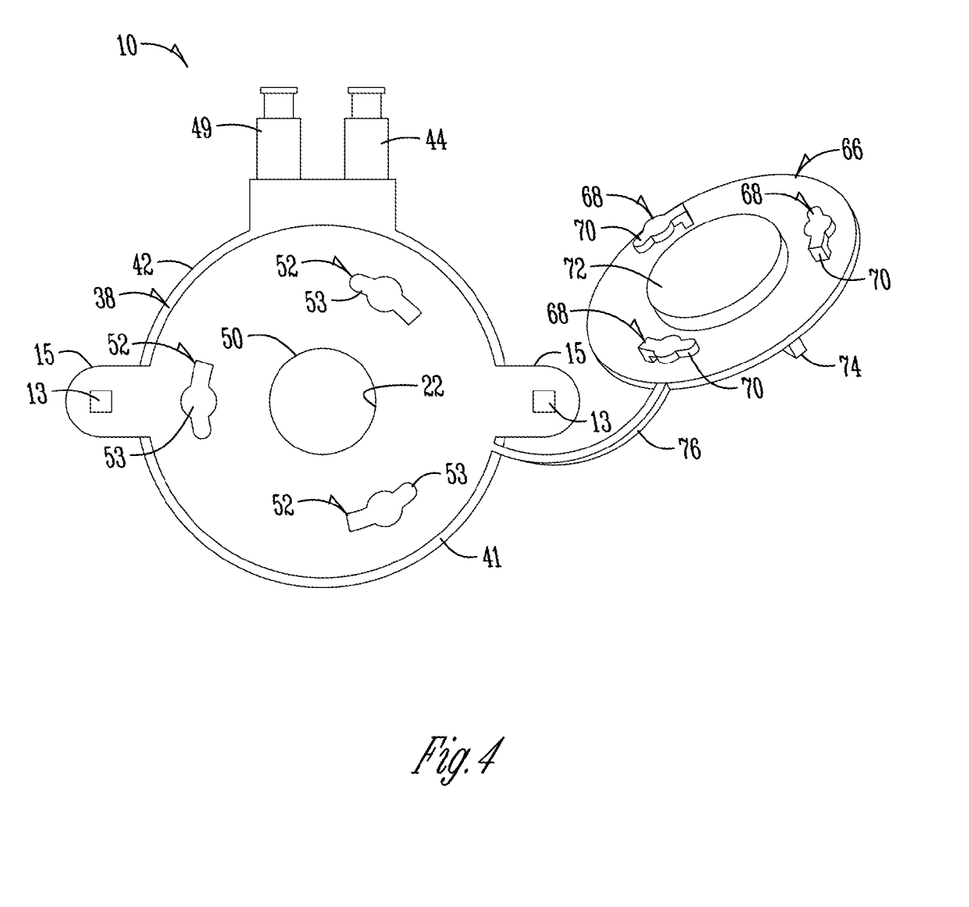
FIG. 4 is an end elevation view of the flow control device.

In FIG. 4, a device adapter 38 is provided either in the wafer 42 or attached to the outer end 18 of the tubular member 14, or attached to the outer surface 41 of wafer 42. The device adapter 38 or wafer 42 includes laterally outwardly extending tube portions 46 and 48 terminating at our near the outer peripheral edge of the wafer 42 or bag adapter 38 in self-sealing micro valves 44 and 49, such as check valves (see FIG. 3). The tube portions 46 and 48 connect respectively to passageway 24 and 32 in the side wall 22 for inflating and deflating the balloon valve 20 and expandable membrane 28 respectively, using for example a syringe. The device adapter 38 has a generally planar outer surface and includes an aperture 50 coinciding with the outer end 18 of the tubular member 14. Spaced radially in, on or through the device adapter 38 is a plurality of interlocking features 52. In a preferred form of this invention, the interlocking features 52 include one or more geometries that provide a twist and lock type connection. In one aspect, the interlocking features 52 include a plurality of keyways 53 radially spaced about the aperture 50 in the device adapter 38.

The device 10 may include a cap 66 having counterpoising interlocking feature 68 radially spaced about a plug 72 sized to occupy the aperture 50 in the device adapter 38 when the cap 66 is secured to the device adapter 38. The counterpoising interlocking features 68 preferably include a plurality of one or more geometries configured to interlock, such as by use of a twist and lock action, with the interlocking features 52 of the device adapter 38 by gripping the rib 74 on the flow control device cap 66, joining the interlocking features 52 and 68 together, and twisting the cap 66 to lock the cap 66 to the device adapter 38. In one aspect of this invention, the counterpoising interlocking feature 68 on the cap 66 include a plurality of keys 70 radially spaced about plug 72. The keys 70 provide a male contact having geometries commensurate with the counterpoising female contacts configured in the device adapter 38 so that the keys 70 are received within the keyways 53 to removably lock cap 66 over the aperture 50 of device adapter 38. A tether 76 may be included on the device adapter 38 attached to cap 66 for keeping it tethered to the adapter 38 when not in use. The interlocking features 52 and 66 in the adapter 38 and cap 66 prevent the cap from inadvertently or accidentally becoming separated from the adapter 38. This invention contemplates that the female or male configuration of the interlocking features 52 and 68 may be switched between the adapter 38 and the cap 66.

Figure 5:
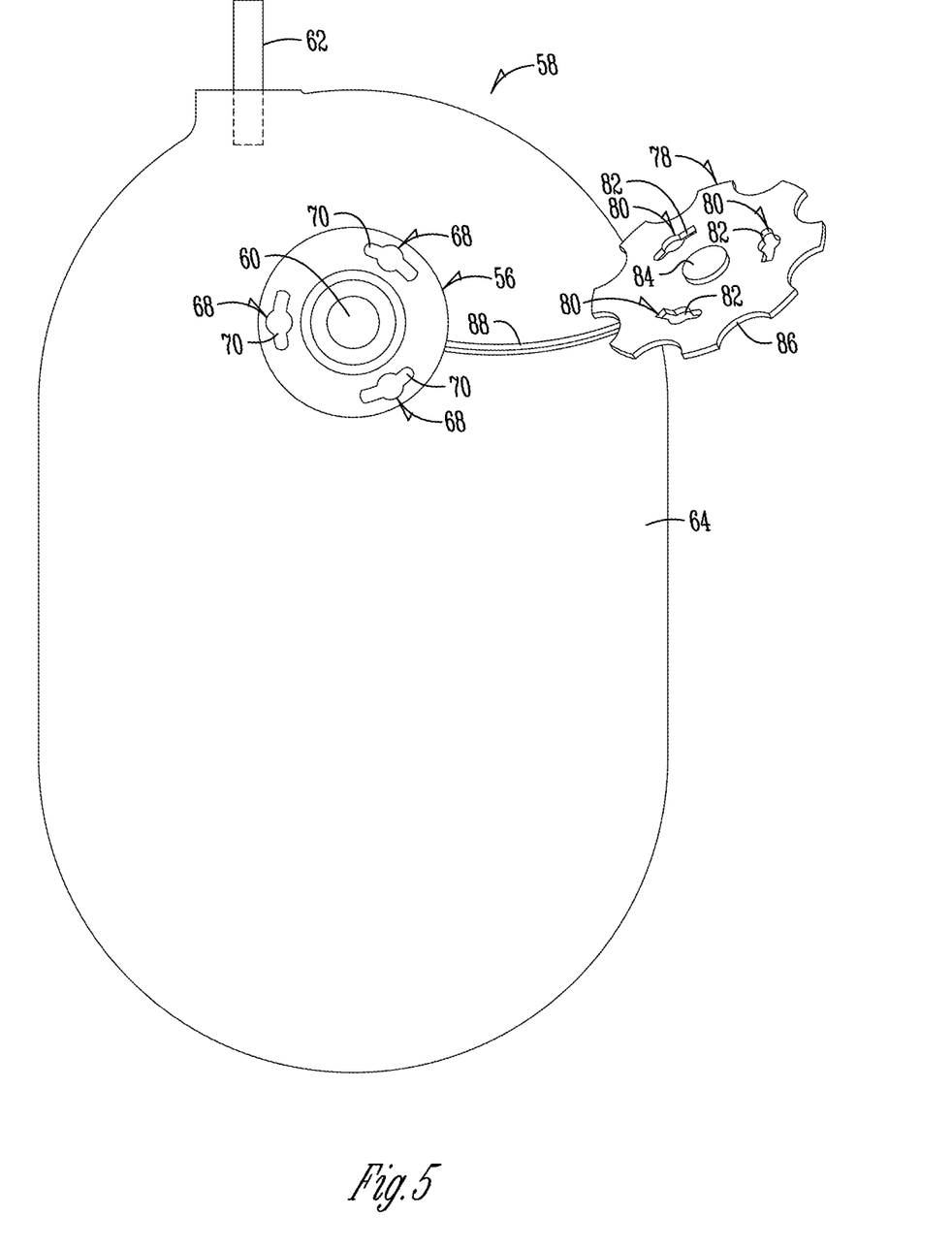
FIG. 5 is a front elevation view of a collection bag of this invention.
Figure 6:
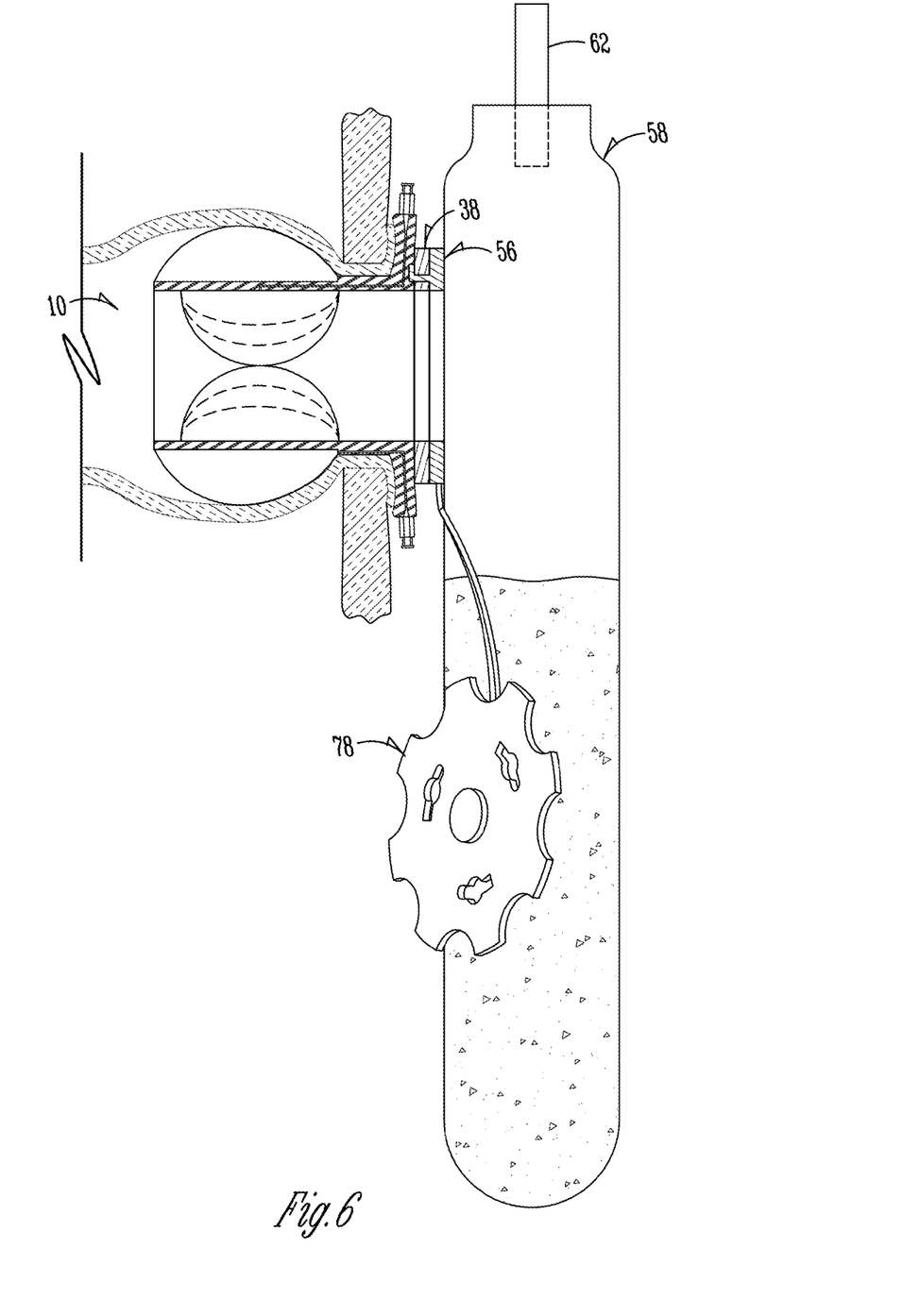
FIG. 6 is a view similar to FIG. 3 but showing adapters connecting the flow control device and waste collection bag.

A waste collection bag 58 is illustrated in FIGS. 5-6. The waste collection bag 58 is formed of a disposable sealed body 64. The sealed body 64 may include a vent 62 for allowing gases to vent from the body. The bag 58 also includes a central opening 60 surrounding circumferentially by a bag adapter 56. The bag adapter 56 is a generally planar wafer-shaped member and may be included in or attached to the sealed body 64 of the bag 58. The bag adapter 56 is also preferably a semi or fully rigid component, and hence constructed of a semi or fully rigid material. The adapter 56 is preferably more rigid than the bag 58 material. Spaced radially about opening 60 either in or on the bag adapter 56 is a plurality of counterpoising interlocking features 68. In one aspect of this invention, the features 68 include a plurality of keys 70 radially spaced about opening 60. The keys 70 are raised a distance off the surface of the adapter 56 to provide a gap between the key and the adapter surface as best illustrated in FIG. 3. The key 70 may include one or more geometries providing a twist and lock function when inserted through a plurality of corresponding keyways, such as the keyways 53 illustrated in the device adapter 38 shown in FIG. 4 or the plurality of keyways 82 shown in the bag cap 78. Although the keys 70 illustrate a specific embodiment of the counterpoising interlocking feature 68 of the present invention, other interlocking features are contemplated. For example, various male and corresponding female features or contacts are contemplated that would allow for a twist and lock function whereby the adapters and caps of the present invention are removably locked together. In another aspect of the invention, the waste collection bag 58 includes a cap 78 that may, in one example, be secured by a tether 88 to the bag adapter 56. The cap 78 includes a plug 84 extending generally perpendicularly and outwardly from the surface of the cap 78 and having a diameter corresponding to the opening 60 in the bag adapter 56. Radially spaced about the plug 84 is a plurality of interlocking features 80. The interlocking features 80, in one aspect of the invention, comprise keyways 82 configured in the bag cap 78. The outer peripheral edge of the cap 78 may include one or more cogs 86 to facilitate gripping, manipulating and turning the cap 78 into a removably locked position onto the bag adapter 56. This is accomplished by aligning the keys 70 of the bag adapter 56 with the keyways 82 in the cap 78, inserting the keys 70 through the keyways 82, and rotating the bag cap 78 either clockwise or counterclockwise depending upon the orientation of the keys 70 on the bag adapter 56. When the cap 78 is removably locked to the bag adapter 56, the plug 84 occupies the spaced defined by opening 60 in the bag adapter 56. The bag 58 is thereby sealed and may be disposed of. Gas venting membranes may be included within vent 62, or in a vent-type plug 84. The membrane may comprise a charcoal filter for filtering and deodorizing gases escaping from the bag 58. In another aspect of the invention, the waste collection bag 58 includes an entirely sealed body 64 having only the single opening 60 in the bag adapter 56. The bag cap 78 includes a filter, such as for example within an opening in the plug 84, to allow gases to escape from the bag 58 through the opening in the plug 84. As illustrated in FIG. 6, the bag adapter 56 mates flush with the device adapter 38 on the flow control device 10. The counterpoising interlocking feature 68 of the bag adapter 56 engage the interlocking features 52 in the device adapter 38. The bag 58 is rotated to thereby removably lock the adapters 56 and 38 together, thereby placing the flow control device 10 in communication with the opening 60 in bag 58. The balloon valve 20 is deflated and waste material and fluids are permitted to flow from the body through the flow control device 10 into the waste collection bag 58. The balloon valve 20 is reinflated to close the device 10 and the waste collection bag 58 is disconnected from the flow control device 10; the flow control device cap 66 may also be used to cap off the flow control device 10.

Figure 7:
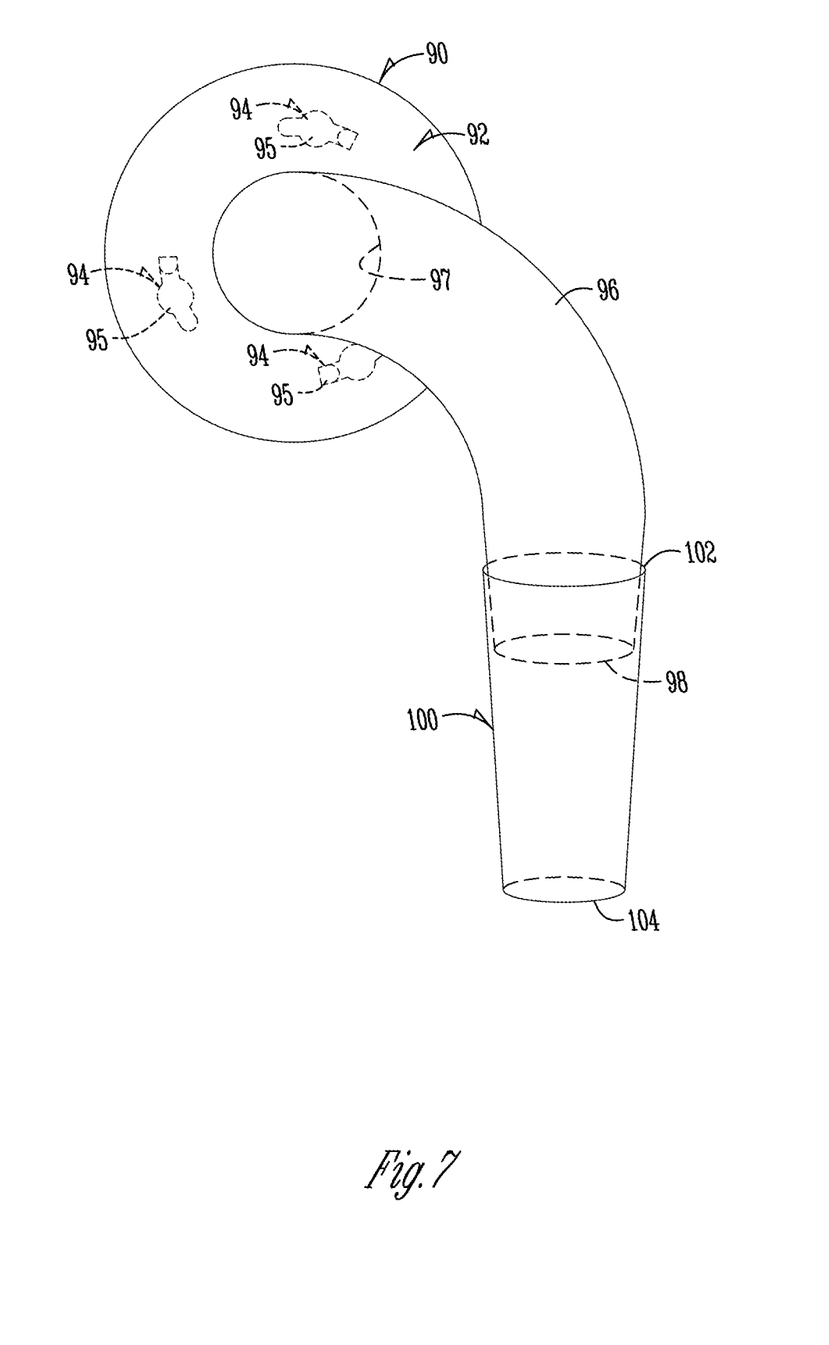
FIG. 7 is a perspective view of a bagless device of this invention.

A bagless device 90 suitable for removable attachment to the flow control device 10 is shown in FIG. 7. The bagless device 90 includes an adapter 92 having a plurality of counterpoising interlocking features 94 radially disposed about the opening 97. In one aspect of this invention, the counterpoising interlocking feature 94 comprises keyways 95 similar to those discussed above. The bagless device 90 includes an outwardly and downwardly extending tube 96 having an opening or inlet 97 and an outlet end 98. The outlet end 98 is tapered, having a generally smaller diameter than the inlet end 97. A degradable tubular sleeve 100 is provided having an inlet opening 102 and an outlet opening 104. The inlet opening 102 may have a diameter generally larger than the outlet end 98 of tube 96 but smaller than the overall average diameter of the tube 96 so as to form a friction fit between the inlet opening 102 of the degradable tubular sleeve 100 and the outlet end 98 of tube 96 when the inlet opening 102 of the sleeve 100 is slid over the outlet end 98 of tube 96. The sleeve 100 may have the same diameter inlet opening 102 as the outlet opening 104 so that the inlet opening 102 is slightly deformed, such as by stretching, to secure it to the outlet end 98 of tube 96. In use, the counterpoising interlocking features 94 mate with the interlocking features 52 of the device adapter 38 (illustrated in FIG. 4). Thus, the bagless device 90 twists and removably locks to the flow control device 10 to allow material and fluid to pass through the flow control device 10, flange tube device 90 and disposable tubular sleeve 100. The sleeve 100 is sufficiently flexible to allow manipulation of the outlet opening 104 to a desired location for dispensing waste material and fluids into a device such as a toilet when standing or seated. The tubular sleeve 100 may be disposed of after each use and the flange tube device 90 cleansed and sanitized for subsequent use.

Figure 8:
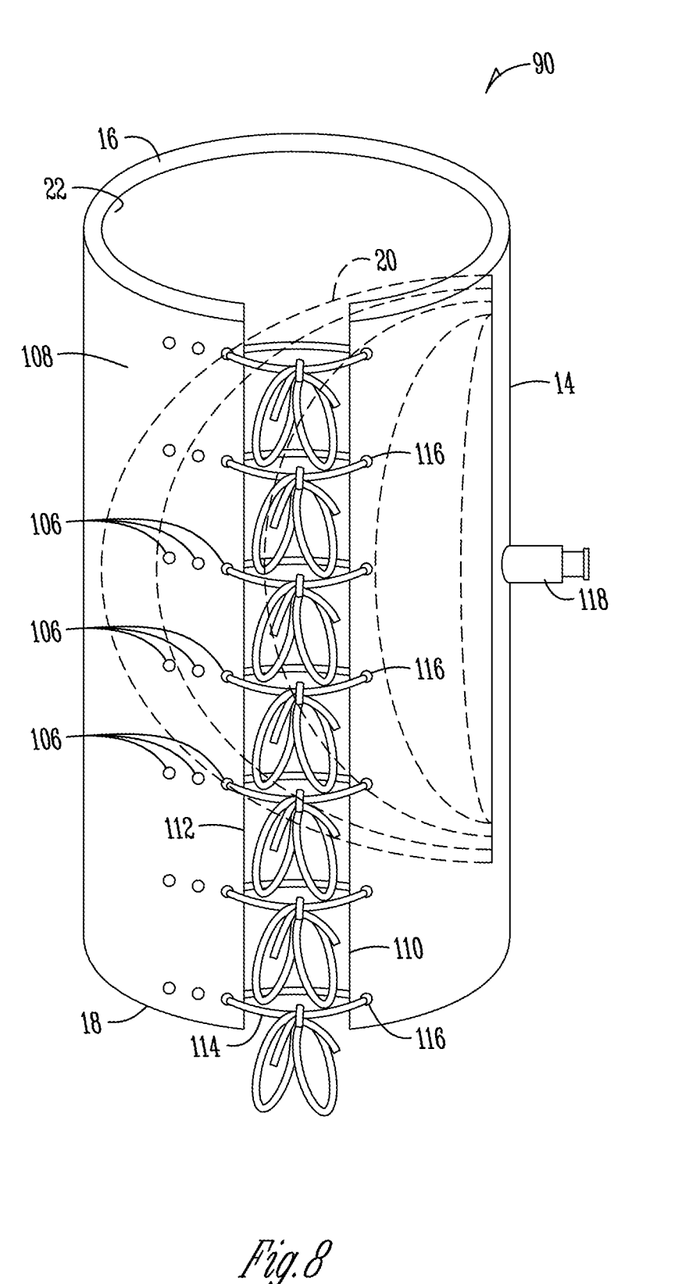
FIG. 8 is a perspective view of another flow control device of this invention for surgical attachment at a body opening.

FIG. 8 discloses another aspect of the present invention. The flow control device 10 illustrated in FIG. 8 includes a tubular member 14 with an opening passing through the entirety of the side wall 108 to allow the diameter of the tubular member 14 to be adjusted to a larger or smaller opening diameter at the inner end 16 and/or outer end 18. Opposing sides 110 and 112 of the side wall 108 include a column of eyelets 116 proximate side 110 and a plurality of adjustment points 106 comprising a plurality of eyelets 116 generally adjacent the opposing side 112. The eyelets 116 and adjustment points 106 on opposing sides 110 and 112 of the side wall 108 are configured generally horizontal relative to each other. A plurality of tethers 114, such as surgical suture, pass through the eyelets 116 and adjustment points 106 to drawn the opposing sides 110 and 112 of the side wall 108 together depending upon the desired size of the opening for the inner end 16 of tubular member 14. Adjustment points 106 allow the diameter of the tubular member 14 to be increased or decreased accordingly. The interior side wall 22 of the tubular member 14 includes a balloon valve 20, as previously discussed, in communication with a passageway terminating externally in a check valve 118. In use, the inner end 16 of the flow control device 10 is surgically attached about a body opening, such as the rectum of the person. Depending upon the size of the rectum of the individual, proper adjustments are made to the diameter of the inner end 16 of tubular member 14 to encircle the rectum with the inner end 16 of the flow control device 10. Tethers 114 are adjusted to size the tubular member 14 accordingly. Inflation and deflation of the balloon valve 20 provides obstruction to and passage of matter and fluids passing from the rectum.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A flow control and collection system for human excretions comprising:
   a flow control device comprising:
   a) a tubular member having an inner end and an outer end interconnected by a passageway, and a wafer extending radially from and integral with the outer end, the tubular member being adapted for insertion into a body opening;
   b) a device adapter having a substantially planar portion positioned adjacent to the integral wafer, and one or more interlocking features, wherein the interlocking features comprise a plurality of radially spaced keyways extending through the substantially planar portion of the device adapter;
   a collection bag comprising:
   a) a sealed body having at least one opening;
   b) a bag adapter at the opening having a substantially planar portion positioned adjacent to the device adapter, and one or more counterpoising interlocking features, wherein the counterpoising interlocking features comprise a plurality of radially spaced keys;
   c) wherein the interlocking features on the device adapter and counterpoising interlocking features on the bag adapter are connected when the plurality of radially spaced keys are joined with the plurality of radially spaced keyways to removably lock the flow control device and collection bag; and
   a collection bag cap selectively sealing the at least one opening of the collection bag, wherein the collection bag cap has a plurality of radially spaced keyways arranged in a same configuration as the plurality of radially spaced keyways of the device adapter.

2. The system of claim 1 wherein the flow control device further comprises an inflatable balloon valve attached within the passageway for selectively allowing passage of matter and/or fluids, the inflatable balloon having a sealing surface that expands radially inward away from a sidewall surface of the passageway to seal together at a center of the passageway.

3. The system of claim 1 wherein the flow control device further comprises an expandable membrane on the outside of the inner end of the tubular member for selectively securing the control device in the body opening.

4. The system of claim 3 wherein the expandable membrane further comprises a wire frame having a collapsed position for inserting the inner end of the tubular member into the body opening and a pre-collapsed position for supporting the tubular member when the expendable membrane is inflated.

5. The system of claim 1 wherein the device adapter comprises an inner surface adjacent the outer end of the tubular member having a concave shape to prevent compression of tissue around the body opening.

6. The system of claim 1 wherein the collection bag cap is connected to the collection bag via a tether.

7. The system of claim 1 wherein the flow control device further comprises a device cap operably connectable to the device adapter to selectively seal the passageway of the flow control device proximate to the outer end of the tubular member, wherein the device cap has a plurality of radially spaced keys arranged in the same configuration as the plurality of radially spaced keys of the bag adapter of the collection bag.

8. A flow control and collection system for human excretions comprising:
 a flow control device comprising:
  a) a tubular member having an inner end and an outer end interconnected by a passageway, and a wafer extending radially from and integral with the outer end, the tubular member being adapted for insertion into a body opening;
  b) a device adapter at the outer end of the tubular member having a substantially planar portion surrounding the passageway, wherein the substantially planar portion has one or more interlocking features comprising a plurality of radially spaced keyways;
 a collection bag comprising:
  a) a sealed body having at least one opening;
  b) a bag adapter at the opening having a substantially planar portion and one or more counterposing interlocking features comprising a plurality of radially spaced keys on the substantially planar portion of the bag adapter;
 wherein the substantially planar portion of the device adapter is positioned adjacent both the integral wafer and the substantially planar portion of the bag adapter;
 wherein the flow control device and collection bag are configurable between a connected and a disconnected position;
 a collection bag cap selectively sealing the at least one opening of the sealed body of the collection bag, wherein the collection bag cap has counterpoising interlocking features comprising a plurality of radially spaced keyways;
 wherein the plurality of radially spaced keys on the collection bag adapter is configured to independently attach directly to the plurality of radially spaced keyways on both the device adapter and the collection bag cap.

9. The system of claim 8 wherein the plurality of radially spaced keyways of the collection bag cap is arranged in a same configuration as the plurality of radially spaced keyways of the device adapter.

10. The system of claim 8 wherein the plurality of radially spaced keys are integrally formed with the substantially planar portion of the bag adapter.

11. A flow control and collection system for human excretions comprising:
 a flow control device comprising:
  a) a tubular member having a inner end and an outer end interconnected by a passageway and adapted for insertion into a body opening, and a wafer extending radially from and integral with the outer end of the tubular member;
  b) an expandable membrane extending outwardly from an exterior of the tubular member proximate to the inner end of the tubular member;
  c) a device adapter at the outer end of the tubular member having a substantially planar portion external to the passageway with one or more interlocking features, wherein the interlocking features comprise a plurality of radially spaced female contacts;
 a collection bag comprising:
  a) a sealed body having at least one opening;
  b) a bag adapter having a substantially planar flange around the opening, the substantially planar flange having one or more counterposing interlocking features, wherein the counterposing interlocking features comprise a plurality of radially spaced male contacts contoured to the radially spaced female contacts;
 a collection bag cap having a plurality of radially spaced female contacts contoured to the radially spaced male contacts of the collection bag;
 wherein the substantially planar portion of the device adapter is positioned adjacent both the integral wafer and the substantially planar flange of the bag adapter;
 wherein the plurality of radially spaced female contacts of the collection bag cap, the plurality of radially spaced female contacts of the device adapter, and the plurality of radially spaced male contacts of the collection bag are arranged in a same configuration; and
 wherein the flow control device and collection bag is configurable between a connected and a disconnected position wherein the interlocking and counterposing interlocking features connect together between the connected and disconnected positions.

* * * * *